United States Patent [19]

Feitelson et al.

[11] Patent Number: 4,983,525
[45] Date of Patent: Jan. 8, 1991

[54] PLASMIDS DERIVED FROM ACTINOMADURA SPECIES

[75] Inventors: Jerald S. Feitelson, Englewood; William M. Maiese, Montclair, both of N.J.

[73] Assignee: American Cyanamid Company, Stamford, Conn.

[21] Appl. No.: 69,427

[22] Filed: Jul. 2, 1987

[51] Int. Cl.$^5$ .............................................. C12N 15/63
[52] U.S. Cl. .................................. 435/320; 435/252.3; 435/825
[58] Field of Search ................... 435/252.1, 252.3, 320, 435/825; 935/29, 72

[56] References Cited

U.S. PATENT DOCUMENTS

| 4,195,079 | 3/1980 | Celmer et al. | 435/825 |
| 4,375,542 | 3/1983 | Waitz et al. | 536/7.1 |
| 4,468,462 | 8/1984 | Malin et al. | 435/253 |

OTHER PUBLICATIONS

Edward Katz et al., Journal of General Microbology (1983), 129, 2703–2714.

Primary Examiner—Elizabeth C. Weimar
Assistant Examiner—Marian C. Knode
Attorney, Agent, or Firm—Estelle J. Tsevdos

[57] ABSTRACT

Plasmid DNA was isolated from two Actinomadura species and characterized by mapping the sites of restriction endonuclease cleavages and by calculation of total molecular size.

7 Claims, 2 Drawing Sheets 10 cm = 1.0 kb 1.5 cm = 1.0 kb

PLASMIDS DERIVED FROM ACTINOMADURA SPECIES

FIELD OF THE INVENTION

The present invention relates to novel plasmid DNA molecules, specifically to those derived from certain Actinomadura species.

BACKGROUND OF THE INVENTION

Plasmids are among the most useful vectors for cloning homologous or foreign genes in microorganisms. Recombinant DNA technology commonly utilizes these extrachromosomal elements for the isolation and characterization of specific genes, and for the expression of gene products. A great deal of effort has gone into the development of genetically engineered plasmid vectors for the gram-negative organism, *Escherichia coli*, as well as gram-positive organisms, such as *Bacillus subtilis* and *Streptomyces lividans*.

Difficulties have been encountered in transforming plasmids between unrelated species because of narrow host range origins of replication, restriction barriers, or unexpressed drug resistance markers. Thus the best starting point for recombinant DNA vector development is from naturally occurring plasmids from the same or closely related species. The present inventors have been able to isolate plasmids which can be useful vectors for applying recombinant DNA technology to the Actinomadura. Therefore, it is now possible to modify antibiotic producing Actinomadura species to increase antibiotic yield. In addition, it is possible to increase the yields of known antibiotics or to construct hybrid antibiotics by using this important class of microorganisms. In copending application Ser. No. 07/069,330 filed July 2, 1987, there are disclosed specific uses for the plasmids of the present invention. The text of that application is incorporated by reference.

SUMMARY OF THE INVENTION

Figure 1:
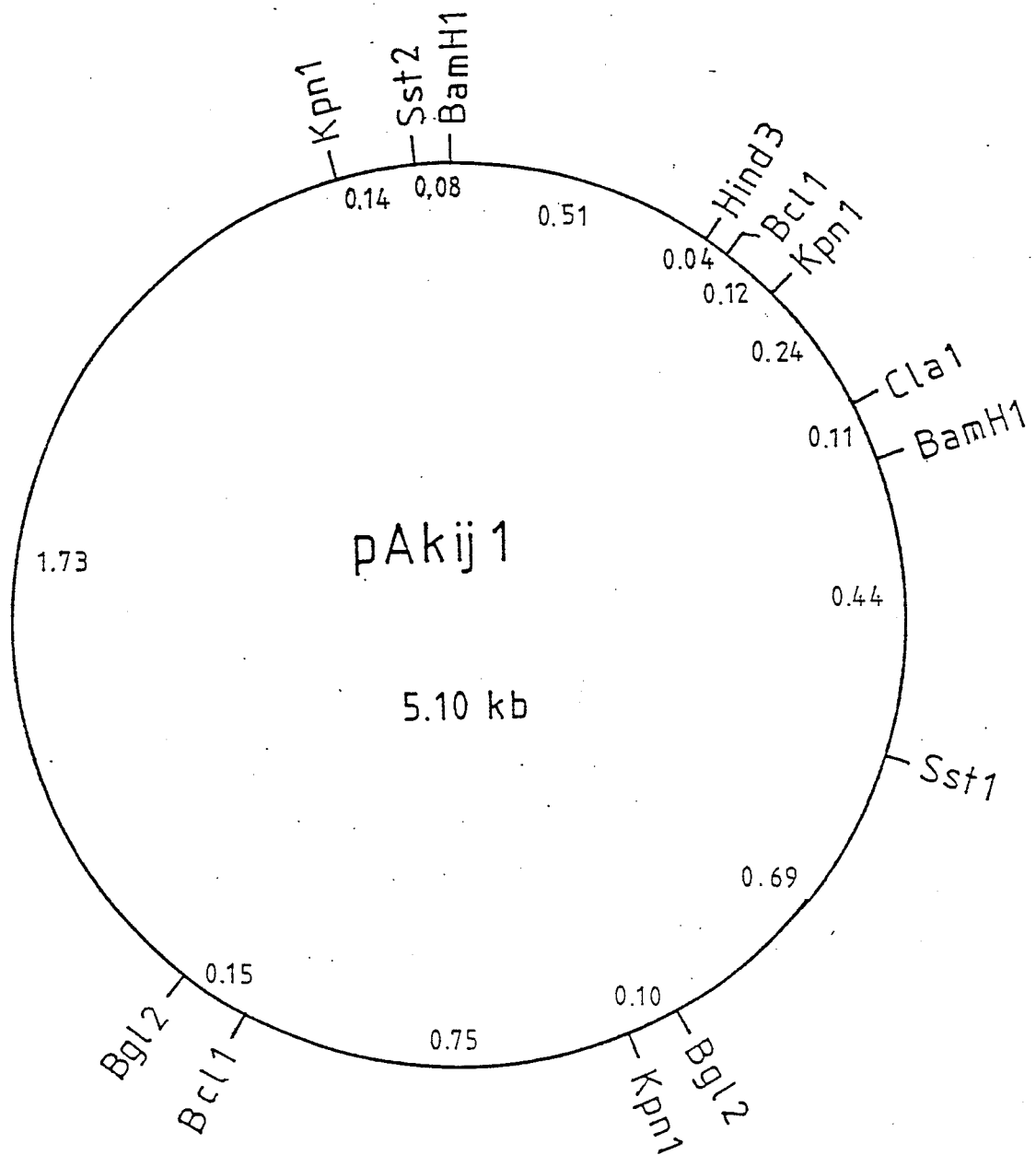
FIG. 1 is a restriction map of the plasmid pAkijl.
Figure 2:
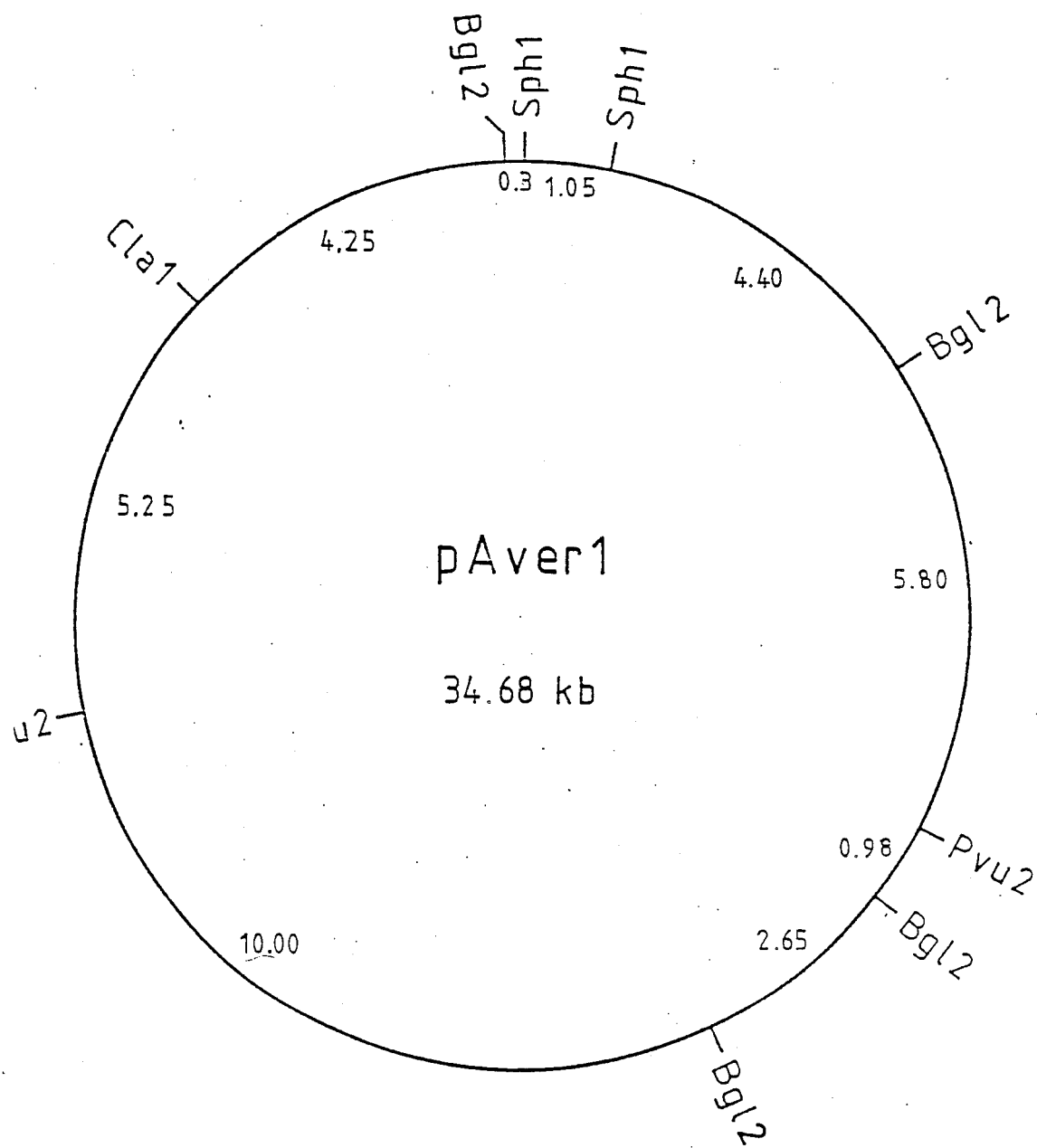
FIG. 2 is a restriciton map of the plasmid pAverl.

The two plasmids of the present invention are characterized by their restriction endonuclease cleavage maps, shown in FIGS. 1 and 2, and by their computed molecular size. Particularly, plasmids named pAkijl and pAverl are preferred. In the drawings, the numerals mean distance between the indicated sites in kilobase pairs (kb) of DNA.

The above described plasmids of the present invention were isolated from the following Actinomycetes, respectively:

pAkijl: *Actinomadura kijaniata* ATCC 31588
pAverl: *Actinomadura verrucosospora* ATCC 27299

Cultures of these species are on deposit at the American Type Culture Collection and they are available to the public.

The plasmids of the invention may be inserted into Actinomycetales, including Actinomadura, using standard procedures as set forth in Hopwood, et al., Genetic Manipulation of Streptomyces, A Laboratory Manual (1985), John Innes, Foundation, Norwich, UK, reference.

DETAILED DESCRIPTION OF THE INVENTION

Example 1

Isolation of plasmid pAkijl from *Actinomadura kijaniata* ATCC 31588 and purification thereof:

Two individual colonies of *Actinomadura kijaniata* ATCC 31588 are inoculated into 15 ml of yeast extract-malt extract broth (YM broth: Difco Co., Michigan) and incubated at 30° C. for 48 hours with shaking at 175 r.p.m. Thereafter, 1.5 ml of seed culture is inoculated into 8 1 L flasks each containing 250 ml of freash YM broth, and grown at 30° C. with shaking at 175 r.p.m. for 48 hours. The mycelia are harvested by centrifugation, washed twice with TE solution (10 mM TRIZMA HCl, 1 mM EDTA, pH8.0), and frozen as a pellet at −20° C. until lysis. Pellets are thawed, and resuspended in 9 volumes of lysis mix containing 10.3% sucrose, 25 mM Tris-HCL, 25 mM EDTA, pH8.0, 2 mg/ml lysozyme. Incubation proceeds at 37° C. for 1 hour. The cells are lysed by addition of 0.6 volumes of 2% SDS - 0.3M NaOH, preheated to 55° C., rapidly mixed, and incubated at 55° C. for 15 min. After cooling the viscous suspension to room temperature, one fourth volume of acid phenol-chloroform mixture (1 g phenol, 1 ml chloroform, 0.2 ml water, 1 mg 8-hydroxyquinoline) is added; mixed for about 5 minutes, and centrifuged at 7000 r.p.m. at 20° C. for 10 minutes. The aqueous supernatant is carefully removed, and sufficient unbuffered sodium acetate is added to give a 0 3M concentration. An equal volume of isopropanol is added, and the nucleic acids precipitated by centrifugation at 12000 x g for 10 minutes at 4C. The pellet is rinsed with −20° C. 70% ethanol, dried, and resuspended in 5 ml TE.

RNaseA (Sigma pancreatic, preheated at 100° C. for 10 minutes) is added to 40 ug/ml, and incubation proceeds at 37° C. for 30 minutes. One extraction with neutral phenol-chloroform (acid phenol-chloroform equilibrated first with 0.5 vol 1M TRIZMA-HCl pH8.8 and then with 0.5 vol 0.1M TRIZMA-HCl pH8.0) is followed by isopropanol precipitation, and DNA is resuspended in 8.0 ml of TE. Cesium chloride (8.47 g) and ethidium bromide (0.403 ml of a 10 mg/ml solution) are added to yield a solution refractive index of 1.3887. After loading a 12 ml Beckman ultracentrifuge tube, density gradient centrifugal separation is carried out at 55,000 r.p.m. at 15° C. for 14 hours, followed by relaxation of the gradient at 38,000 r.p.m. at 15° C. for 8 hours on a Beckman Model L8 ultracentrifuge in an 80ti fixed angle rotor. The centrifuge tube is irradiated with 365nm ultraviolet light and the lower, plasmid band removed with a needle and syringe.

Further, the plasmid solution was recentrifuged at 38,000 r.p.m. at 25° C. for 62 hours, and the plasmid band removed from the gradient as before. After removal of ethidium bromide by chromatography through a pasteur pipette containing Dowex AG 50W-X2 (Bio-Rad), the plasmid DNA is diluted with 2 volumes of TE, and precipitated with ethanol. Final concentration of the purified plasmid DNA preparation is approximately 100 ug/ml.

Restriction mapping of each plasmid is done by conventional mapping techniques, employing single and double restriction enzyme digests as appropriate, followed by agarose gel electrophoresis. Molecular sizes of the resulting DNA segments obtained by restriction enzyme digestion of the plasmid are calculated by measuring their relative mobility to HindIII segments of lambda phage DNA.

Digests are performed by incubating 0.25–1 ug of plasmid DNA with 10 units of restriction enzyme in a 20 ul reaction volume under optimum conditions recommended by the enzyme supplier. The reaction is allowed to proceed for one hour at 37° C., then heated to 70° C. for 10 minutes. After alcohol precipitation, the cleaved DNA is resuspended in 10 ul of TE, 1.1 ul of dye solution (25% Ficoll 40000, 0.025% Orange G) is added, and the analysis carried out by agarose gel electrophoresis. Namely, a 0.7% or 1% agarose gel is used in a Tris-EDTA-Boric acid buffer solution (89 mM Tris, 2.5 mM EDTA, 89 mM Boric acid), and electrophoresis in a horizontal submarine gel is performed at 150 volts for approximately 1¼ to 1¾ hours at approximately 100 mAmps. The gel is stained in a 0.5 ug/ml solution of ethidium bromide for 10 minutes followed by destaining in distilled water for 5 minutes. A photograph of the gel is taken using Polaroid Type 57 film through a Wratten gelatin filter and UV Products transilluminator.

The restriction map of pAkijl is shown in FIG. 1.

There were no restriction enzyme cleavage sites in pAkijl for the following enzymes: EcoR1, EcoR5, Pst1, Pvu2, Sph1, Xbo1, and Xho1.

There were additional unmapped restriction enzyme cleavage sites in pAkijl as follows: SalG1, 3; Smal, 4.

The computed molecular size of pAkijl is approximately 5,100 base pairs.

Example 2

Isolation of plasmid pAverl from *Actinomadura verrucosospora* ATCC 27299 and purification thereof:

Isolation of a plasmid from *Actinomadura verrucosospora* ATCC 27299 and purification thereof are carried out by the same procedure as in Example 1.

Measurement of the molecular size and construction of the restriction map are carried out by the same procedure as in Example 1. Results are shown in FIG. 2.

There are no restriction enzyme cleavage sites in pAverl for the following enzymes: EcoR1, EcoR5, HindIII, PstI, Xab1 and Xho1.

There were additional unmapped restriction enzyme cleavage sites in pAverl as follows: BamHl, 10; Kpnl, 6; SalGl, 15; Smal, 15; Sstl, 15, Sst2, 15.

The computed molecular size of pAverl is approximately 34,700 base pairs.

All of the listed applications and references are incorporated by reference.

While the invention has been described in detail and with reference to specific embodiments thereof, it will be apparent to one skilled in the art that various changes and modification can be made therein without departing from the spirit and scope therein.

We claim:

1. An isolated essentially pure plasmid derived from Actinomadura having at least one restriction cleavage site for specific restriction enzymes and a molecular size of less than 40,000 base pairs of DNA, wherein said plasmids are selected from the group consisting of pAkijl and pAverl.

2. A plasmid as defined in claim 1 which is obtained from *Actinomadura kijaniata*.

3. A plasmid as defined in claim 2 which is obtained from *Actinomadura kijaniata* ATCC 31588.

4. A plasmid as defined in claim 1 which is obtained from *Actinomadura verrucosospora*.

5. A plasmid as defined in claim 4 which is obtained from Actinomadura verrucosospora ATCC 27299.

6. The plasmid according to claim 1 which is pAkihl.

7. The plasmid according to claim 1 which is pAverl.

* * * * *